(12) United States Patent
Kuvshinov et al.

(10) Patent No.: US 7,238,853 B2
(45) Date of Patent: Jul. 3, 2007

(54) MOLECULAR MECHANISMS FOR GENE CONTAINMENT IN PLANTS

(75) Inventors: Viktor Kuvshinov, Helsinki (FI); Kimmo Koivu, Helsinki (FI); Anne Kanerva, Helsinki (FI); Andrei Anissimov, Helsinki (FI)

(73) Assignee: Unicrop Ltd, Helsinki (FI)

( * ) Notice: Subject to any disclaimer, the term of this patent is extended or adjusted under 35 U.S.C. 154(b) by 314 days.

(21) Appl. No.: 10/644,664

(22) Filed: Aug. 20, 2003

(65) Prior Publication Data

US 2004/0107457 A1  Jun. 3, 2004

Related U.S. Application Data

(63) Continuation-in-part of application No. 09/617,543, filed on Jul. 14, 2000, now Pat. No. 6,849,776.

(51) Int. Cl.
*C12N 15/82* (2006.01)
*C12N 5/04* (2006.01)
*C12N 5/10* (2006.01)
*A01H 5/00* (2006.01)
C12N 15/31 (2006.01)
C12N 15/55 (2006.01)
A01H 1/02 (2006.01)

(52) U.S. Cl. ............ 800/271; 800/278; 800/287; 800/288; 800/290; 435/199; 435/320.1; 435/419; 536/23.7; 536/24.1

(58) Field of Classification Search ............ 800/278, 800/287, 288, 290, 271, 303; 435/199, 320.1, 435/419; 536/23.7, 24.1
See application file for complete search history.

(56) References Cited

OTHER PUBLICATIONS

Kriete et al. The Plant Journal 9(6): 809-818 (1996).*
Williams, M. Trends in Biotechnology 13: 344-349 (Sep. 1995).*
Kuvshinov et al. (2004) Barnase gene inserted in the intron of GUS . . . Plant Science 167: 173-182.
Edgell, D. et al. Barriers to Intron Promiscuity in Bacteria. (2000) J. Bacteriology 1282(19) 5281-5289.
Schernthaner J. (2003) Control of seed germination in transgenic plants . . . PNAS vol. 100 No. 11. pp. 685-6859.
Gressel 1999: Tandem constructs: preventing the rise of superweeds. TIBTECH vol. 17 pp. 361-366.
Daniell H. (2002) Molecular strategies for gene containment in transgenic crops. Nature biotec, 20 pp. 581-586.

* cited by examiner

*Primary Examiner*—David T. Fox
(74) *Attorney, Agent, or Firm*—Dodds and Associates

(57) ABSTRACT

The present invention provides a molecular mechanism for gene containment in sexually reproducing transgenic plants. The mechanism is achieved with a molecular construct comprising a blocking construct (BC) that is inserted fully or partially into an intron of a transgene of interest (TGI). The TGI encodes desired gene products, such as heterologous or homologous proteins, peptides or other useful products. The expression of the BC leads to block of at least one molecular or physiological function that is essential for development or reproduction of the transgenic plant. Thereby the BC expression leads to death or incapacity of sexual reproduction of the plant. Moreover, the mechanism comprises an externally applicable recovering tool to recover the functions blocked by the BC. The recovering tool may be a recovering construct (RC).

20 Claims, 14 Drawing Sheets

A
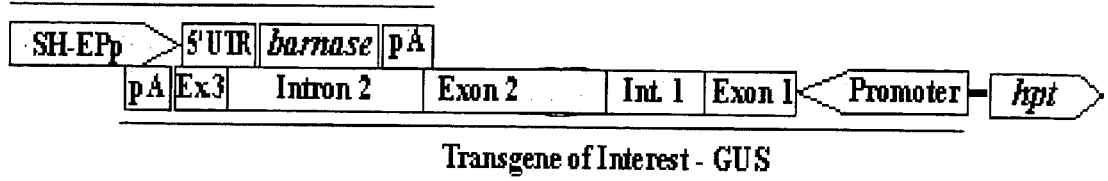
B
C
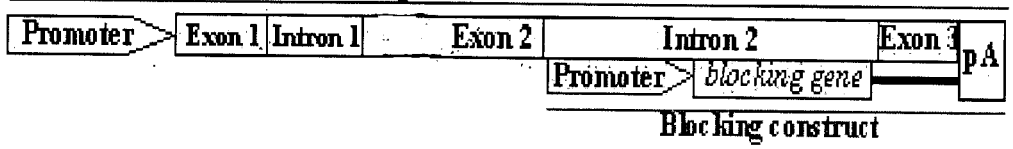
FIG. 1

```
Barnase                                                                                                              uidA
gene nt    >SH-EP promoter from Vigna mungo>          >CAAT box>                                                     gene nt
    ↓↓...TATTGAATCCTTGGCTACCATTCTTGAGAAACACCAAACACTTCTTATATCGTTCTACACAATTCTCTGAGTGCGTGCCACAGTTTGGTATCTTCATGATTGCTCATTGTTCATGCCCA    ↓↓
-302 ---+---------+---------+---------+---------+---------+---------+---------+---------+---------+---------+---------+ 2331
    ...ATAACTTAGGAACCGATGGTAAGAACTCTTTGTTTGTTTGTGAAGAATATAGACAAGATGTGTTAAGAGACTCACGCACGGTGTCAAACCATAGAAGTACTAACGAGTAACAAGTACGGGT
                                                                                                  PolyA cleavage↑
>CAAT box>
        TAAGGAACATGTAACTTCCTCATTTATTTATTATTGCTTTTGTTTTCTTCTCACTAGTTTACAAACGTTTCCCTATATAAACCCTCCTTTGTTCACTGCTTCTCCCCTGCTGGCTTC
                                                              SpeI      > TATA box >
-182 ---+---------+---------+---------+---------+---------+---------+---------+---------+---------+---------+---------+ 2211
        ATTCCTTGTACATTGAAGGAGTAAATAATAATAACGAAAACAAAAGAAGAGTGATCAAATGTTTGCAAAGGGATATATATTTGGGAGAAACAAGTGACGAAAGGAGGACGACCACCGAAG
           <NUE < NUE<                                        <FUE<                                Stop<  uidA
    >  >5'UTR                        +1 Start of barnase>
        TCTCCGAAGTTCATCCCGGTCCACCTGCAAATAAGTAAATAAGATAAAAGTAAAAAGTTAGTATGGCTCAAGTTATTAATACTTTTGATGGAGTTGCTGATTATCTTCAAACTTATCATA
-62 ---+---------+---------+---------+---------+---------+---------+---------+---------+---------+---------+---------+ 2091
        AGAGGCTTCAAGTAGGGCCAGGTGGACGTTTATTCATTATTCTATTTCATTTTTCAATCATACCGAGTTCAATAATTATGAAAACTACCTCAAGCACTAATAGAAGTTTGAATAGTAT
        3ᵈ exon of uidA    ↑3'intron<       <branch point<                                     intron of uidA AACTTCCAGATAATTATATTACTAAATCTGAAGCTCAAGCTTCTTGGATGGTTGCTCTCTAAAGGAAAATCTATTGGAGGAGATATTTTTCAAATA
+59 ---+---------+---------+---------+---------+---------+---------+---------+---------+---------+---------+---------+ 1971
        TTGAAGGTCTATTAATAATAATGATTTAGACTTCGAGTTCGAGAGATTCCTTTAGAAACGACTACACGAGGTCCTTTAGATAACCTCCTCTATAAAAAGTTTAT EcoRI
        GAGAAGGAAAACTTCCAGGAAAATCTGGAAGAACATGGAAGAGAGAAGCTGATATTAATTATACTTCTGGATTTAGAAATTCAGATAGAATTCTTTATTCATCTGATTGGCTTATTATAAAA
+179 ---+---------+---------+---------+---------+---------+---------+---------+---------+---------+---------+---------+ 1851
        CTCTTCCTTTTGAAGGTCCTTTTAGACCTTCTTGTACCCTCTCTTCGACTATAATTAATAATGAAGACCTAAATCTTTAAGTCTATCTTAAGAAATAAGACTAACGAATAAATATTTT
          barnase>        >Stop>  >FUE>  >FUE>   BclI    >NUE>            PstI PolyA cleavage
        CTACAGATCATTATCAAACTTTTACAAAAATTAGATAAATATTTGTATTTTTTGTATGTGTGATCATTAATAATAAATACATCCTCTTCTGCAGCAGGAAGGCAGCCGA...   ...
+299 ---+---------+---------+---------+---------+---------+---------+---------+---------+---------+---------+---------+ 1735
        GATGTCTAGTAATAGTTTGAAAATGTTTTAATCTATTATAAACATAAAAAACATACAACACTAGTAATTATTTATTTATTTATGTATGGAGAAGACCTGTCCTTCCGTCGGCT...   ...
        <2ᵈ intron of uidA                 <5'intron↑                         2ᵈ exon of uidA

FIG 2.
```

MOLECULAR MECHANISMS FOR GENE CONTAINMENT IN PLANTS

CROSS-REFERENCE TO RELATED APPLICATIONS

This application is a continuation-in-part of application Ser. No. 09/617,543 filed 14 Jul. 2000, now U.S. Pat. No. 6,849,776.

SEQUENCE DATA

This application contains sequence data provided on a computer readable diskette and as a paper version. The paper version of the sequence data is identical to the data provided on diskette

TECHNICAL FIELD

This invention relates, in general, to containment of plant germplasm and, in particular to a method and a DNA construct for controlling segregation of transgenes in plants.

BACKGROUND

The techniques of plant biotechnology have improved during the last ten years so that most of the crop species important to the mankind can be transformed today. This has led to a situation where a continuously increasing number of crop species have been transformed with a continuously increasing number of traits. This together with the concerns of environmental impacts of genetically modified (GM) crops has created a clear need for a new generation of GM-crops having a reduced probability of transgene flow among crops and their relatives. Accordingly, several research groups around the world are currently engaged in developing techniques for gene containment in transgenic crops. Henry Daniel 2002 (Molecular Strategies for Gene Containment in Transgenic Crops. Nature Biotech 20: 591–585) gives a good review of the techniques available today.

The molecular approaches for control of transgene flow can basically be divided into to two groups: one-factor systems and two-factor systems. The one-factor techniques use a negative selection factor to prevent any plant carrying the transgene to interbreed with wild type relatives or with their own offspring. Examples of one-factor technologies are male sterility described in U.S. patent application No. US2002157129, chloroplast transformation described by Scott and Wilkinson in Nat. Biotechnol. 17. 390–392 (1999), technology launched by Monsanto and known as 'terminator technology' described in U.S. Pat. No. 5,723,765 and tandem mitigation concept described by Gressel in Trend in Biotech. 17: 361–366.

The main limitation of one-factor techniques is that they may not offer absolute transgene containment. The negative selection eliminates transgene from population of plants in course of several generations. Acting as a negative selection factor, male sterility and chloroplast transformation decrease the reproduction capacity of transgenic plants by limiting pollen spread. These methods however, do not prevent transgene flow through seed shatter. The 'terminator' technology prevents gene flow only when killer (or terminator) gene is activated. After the activation of killer gene (negative selection factor) seeds of the next progeny are incapable to germinate and, therefore the plants cannot be propagated further. If the killer gene is not activated the transgene insert can freely flow because the killer gene remains silent.

The idea of tandem mitigation technology is to use genes, which are adverse for wild plants but neutral for cultured transgenic relatives. Because there are no genes absolutely perfect for such purposes, the technology can only exploit genes that reduce the vitality/reproductivity of wild relatives carrying the transgene insert. Therefore the limitation of this technology is that several generations are needed to remove the transgene from population.

Recently, two-factor concepts of molecular control have been proposed to significantly reduce a probability of transgene introgression into a population of sexually compatible plants.

Basically two-factor technologies use the negative selection factor (BC or EC), which absolutely prevents the transgene flow. This is made possible by using another rescuing factor, which represses the action of the first factor, disrupt killer gene or recovers the blocked function of the plant.

International patent publication WO9403619 (Bright et al.) describes a method, where disrupter gene (negative selection factor—BC) disrupts the transgene of interest or its promoter (by Cre recombinase) or kills the plant. Chemically inducible repressor gene represses the promoter of disrupter gene.

International patent publication WO0037660 (Fabijanski et al.) describes the system where lethal gene (BC) is linked to a transgene of interest. Repressor gene (RC) is placed into another allelic (sister) or non-allelic chromosome. Second pair of lethal and repressor genes can be placed in opposite order in the same inserts.

International patent publication WO02064801 (Kuvhshinov et al.) describes a system, where Excision construct EC is linked to the TGI. The EC excises the whole insert from the genome of the host organism under natural conditions. Artificially activated repression construct RC represses the action of the EC and saves the transgenic insert in the host genome. This system removes the entire transgene insert and leaves the host genome free from the foreign genes. Thus, transgenic plants can produce non-transgenic seeds.

Although the described prior art gives advanced alternatives to control transgene flow, none of the prior art resolves the problem of BC being inactivated by mutagenesis. This can happen approximately with a frequency of $10^{-6}$. In practice this means once in each middle size field plot during a growth season. The present invention markedly decreases the probability of BC to become inactivated.

U.S. patent application Ser. No. 09/617,543 (Kuvshinov et al.) discloses a two-factor system called RBF (recoverable block of function) system. RBF system comprises a blocking construct (BC) linked to a transgene of interest (TGI) and a recovering construct (RC). According to this invention BC blocks a vital physiological or molecular function of the host plant through developmental or organ specific expression. The RC is induced by an externally controllable stimulus and when induced it recovers the function previously blocked by the BC. Even if this system is a huge step ahead in transgene containment techniques it as such does not remove the possibility of reorganization of genomic DNA in the segregating progenies.

This problem is resolved with the invention according to the present disclosure. The present invention minimizes reorganization of genomic DNA in a RBF system similar to that described in U.S. patent application Ser. No. 09/617,543 now U.S. Pat. No. 6,849,776.

According to the present disclosure the BC is placed into an intron of the TGI, thereby providing an inseparable genetic linkage between the BC and the TGI. This arrangement minimizes the probability of crossing-overs between the BC and the TGI and thereby prevents them being segregated.

Furthermore, this arrangement minimizes probability of large mutations of the BC without destroying the TGI simultaneously. Therefore, this disclosure resolves another problem the prior art includes; i.e. mutated BC would probably not block the reproduction of the transgenic plant and therefore the containment of the transgene would be incomplete if the TGI was not destroyed too.

SUMMARY OF INVENTION

An object of the present invention therefore is to provide molecular mechanism for gene containment in sexually reproducing transgenic plants. The mechanism is achieved with a molecular construct comprising a blocking construct (BC) that is inserted fully or partially into an intron of a transgene of interest (TGI). The TGI encodes desired gene products, such as heterologous or homologous proteins, peptides or other useful products. The expression of the BC leads to block of at least one molecular or physiological function that is essential for development or reproduction of the transgenic plant. Thereby the BC expression leads to death or incapacity of sexual reproduction of the plant. Moreover, the mechanism comprises an externally applicable recovering tool to recover the functions blocked by the BC. According to one embodiment of the invention the recovering tool comprises a recovering construct (RC). The RC may be controlled through an inducible promoter.

Also contemplated in the present invention are cloning vectors, cells or cell-lines for convenient preparation of transgenic plants harboring one or more DNA construct complex providing the gene containment according to the present invention. The invention moreover describes synthetic nucleotide sequences adapted for insertion into intron of the TGIs. The characteristic features of the present invention are defined in more detail in the claims

BRIEF DESCRIPTION OF DRAWINGS

FIG. 1. depicts the molecular constructs described in Examples 2 and 3.
  (A) Intron cassette—the two genes are in the same DNA sequence. In Sal construct, GUS gene is expressed under Sal promoter, and Tet construct-under 35S promoter with three tet operators, which are repressed by product of additional tetR gene expressed under 35S promoter.
  (B) Recovering construct in separate insert. Barstar gene is under Heat Shock promoter.
  (C) Position of blocking gene in the same direction with TGI with shared polyadenyalation site.

FIG. 2. Depicts the sequence of the intron cassette described in Examples 2 and 3 (SEQ ID NO:13). From left to right: Blocking construct sequence containing part of SH-EP promoter, 5'UTR, coding sequence and polyA signals of Barnase gene. From right to left is the last part of TGI-uidA (GUS) including end of the second exon, second intron, and the third exon and polyA signals. Underlined nucleotides in the sequence of SH-EP promoter were changed from natural nucleotides, Abbreviations: CAAT and TATA-promoter signal sites, NUE—near upstream element and FUE-far upstream element of polyA; SpeI, EcoRI, BclI and PstI restriction endonuclease sites. Sequences of signal sites are marked by bold face.

TERMS USED IN THE DISCLOSURE

Figure 3:
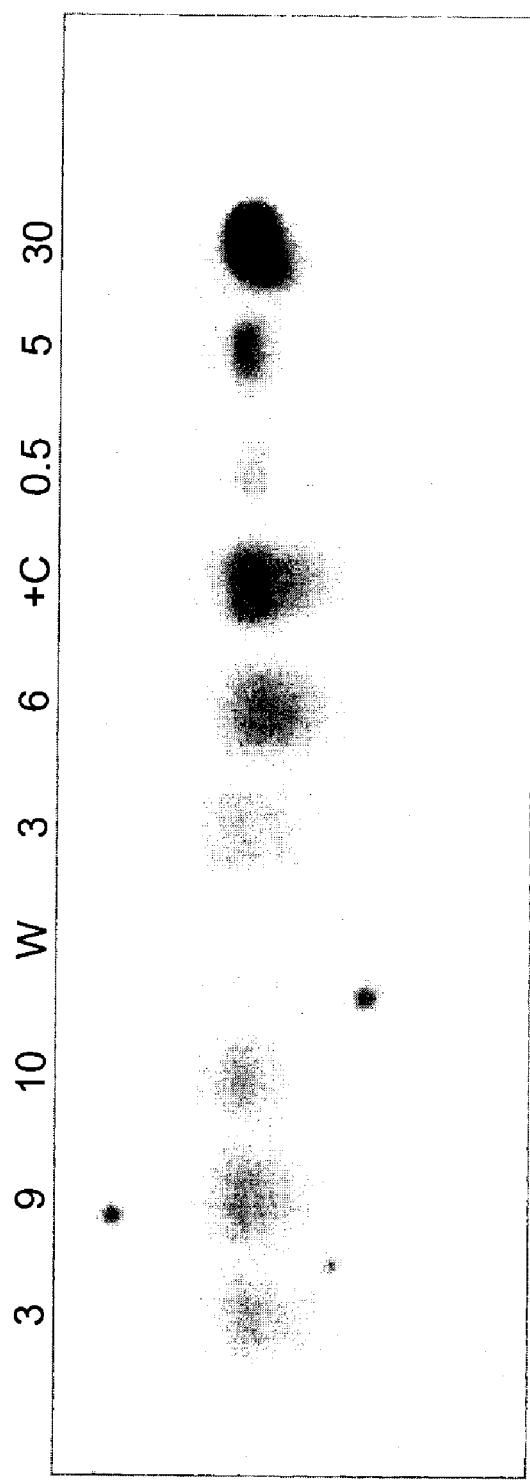
FIG. 3. Northern hybridization of Barstar expression in tobacco plants transformed by pGPTV-KAN-HSpBarstar. The first three lines on left side represent transgenic lines 3, 9 and 10. W, represents the wildtype tobacco RNA. Line 3 and 6 in the middle of the blot express barstar mRNA from 35S promoter. +C represents cold synthetic barstar RNA. The three last lines on the right hand side represent positive controls having 0.5, 5 and 30 pg of synthesized cold RNA of barstar. Plants were incubated at 40° C. for 1 hour.

In the present disclosure most of the terms used have the same meaning as they generally have in the field of recombinant DNA techniques, molecular biology and plant production related sciences. Some terms are, however, used in somewhat different way and are explained in more detail below.

Recoverable block of function (RBF) means a conceptual molecular system comprising a blocking construct (BC) and a recovering tool. The recovering tool may be a recovering construct (RC). RBF performs the control of segregation and prevents the introgression of the transgene(s) of interest (TGIs) into a population of sexually compatible plants. RBF is introduced into the host plant together with the TGIs by a process of genetic transformation.

Segregating RBF system is a RBF, wherein the recovering construct (RC) is situated in a different non-allelic or allelic chromosome apart from the BC and the TGI(s). Accordingly, the blocking function becomes functional in the second heterozygous hybrid generation, when the BC and the RC segregate into different generative cells.

Double RBF means that the TGI(s) is (are) situated between two BCs, which may either be similar or different to each other.

Blocking construct (BC) is a DNA or nucleotide sequence having a capacity to block a particular molecular or physiological function of the host plant. The BC may be expressed constitutively, organ-specifically, development-specifically or spatiotemporally. According to this disclosure the BC is placed into an intron of the TGI.

Recovering tool means a method for recovering the transgenic plant harboring the BC from the detrimental consequences of the expression of the BC. Preferably the recovering tool is a DNA construct or a nucleotide sequence herein called recovering construct (RC).

Recovering construct is a DNA construct or nucleotide (DNA or RNA) sequence, which recovers, unblocks or releases the functions blocked by the expression of the BC. The RC is introduced into the genome of the host plant, separately or together with the BC and the transgene(s) of interest TGI(s). The expression of the RC is initiated only under external intervention. Therefore, the RC is not expressed without an external controllable induction. The external intervention may for example be provided by an outside stimulus of a responsive promoter that drives the RC. The external intervention may also be provided by intraline crossing of transgenic plants to support a homozygous condition of the RBF.

Transgene of interest (TGI) means the DNA or nucleotide sequences, including RNA sequences, which encode a desired gene product; i.e. protein, antibody, enzyme or other substances, including metabolites, hormones, toxins, antibiotics, etc. The TGIs are introduced into the plant genome by the method of genetic transformation.

Blocking is a molecular control mechanism; e.g. nucleotide sequence the expression of which blocks, arrests or inhibits a function essential for the survival, growth, development and/or sexual reproduction of the plant and is capable or arresting the development of the molecular machinery of the host plant at the level of DNA, mRNA, protein or metabolite.

DETAILED DESCRIPTION OF THE PREFERRED EMBODIMENTS

The present disclosure is related to methods of molecular biology for controlling transgene segregation and introgression into a population of sexually compatible plants. The control is achieved through DNA constructs herein called a recoverable block of function (RBF) system. The RBF comprises a BC the expression of which blocks a particular physiological or developmental function of the host plant, which leads to either death of the plant or to such a change in its physiology that the plant is not anymore capable of reproduction.

According to one preferred embodiment of the present disclosure the RBF system comprises also an RC that is capable of recovering the function blocked by the BC. The RC is introduced to the host plant genome separately or together with the BC and TGI. The RC may be placed in the same or different chromosome than the BC and TGI. The RC is externally controlled, i.e. it is expressed only when an external intervention is applied to the system.

According to the present disclosure the RC can be controlled through an inducible promoter. According to one embodiment the inducible promoter to control the RC may be responsive to physical treatment e.g. heat shock. The invention is however, not limited to the use of heat shock inducible promoters but other physically or chemically inducible promoters may be used as well.

According to the present disclosure the BC may be expressed constitutively, organ specifically, spatiotemporally or development stage specifically. According to one embodiment of the present invention the BC is placed under germination specific promoter, such as SH-EP from *Vinga mungo*.

The present disclosure introduces a novel RBF system where the BC is inserted into an intron of the TGI. This approach minimizes the probability of separation of the BC and the TGI. Large mutations of the BC are almost impossible without simultaneously destroying the TGI. Therefore, the present disclosure brings a significant improvement to the field of transgene containment and prevention of transgene segregation and introgression into populations of compatible plants.

The DNA construct of the BC and the RC according to one embodiment of the present invention are synthetic sequences of barnase and barstar genes adapted for plant expression and comprising SEQ ID: NO 1 and SEQ ID: NO 2, respectively.

The RBF models according to this disclosure can be divided into the following types according to the mechanism of action and the construction structure.

Externally Compensated (Simple) RBF

The RBF consists solely of the BC. The BC may be active constitutively, development specifically or organ specifically. The recovering tool comprises external compensation of the required metabolite: amino acid, hormone or some other metabolite. There is no RC in this embodiment.

Segregating RBF

Figure 13:
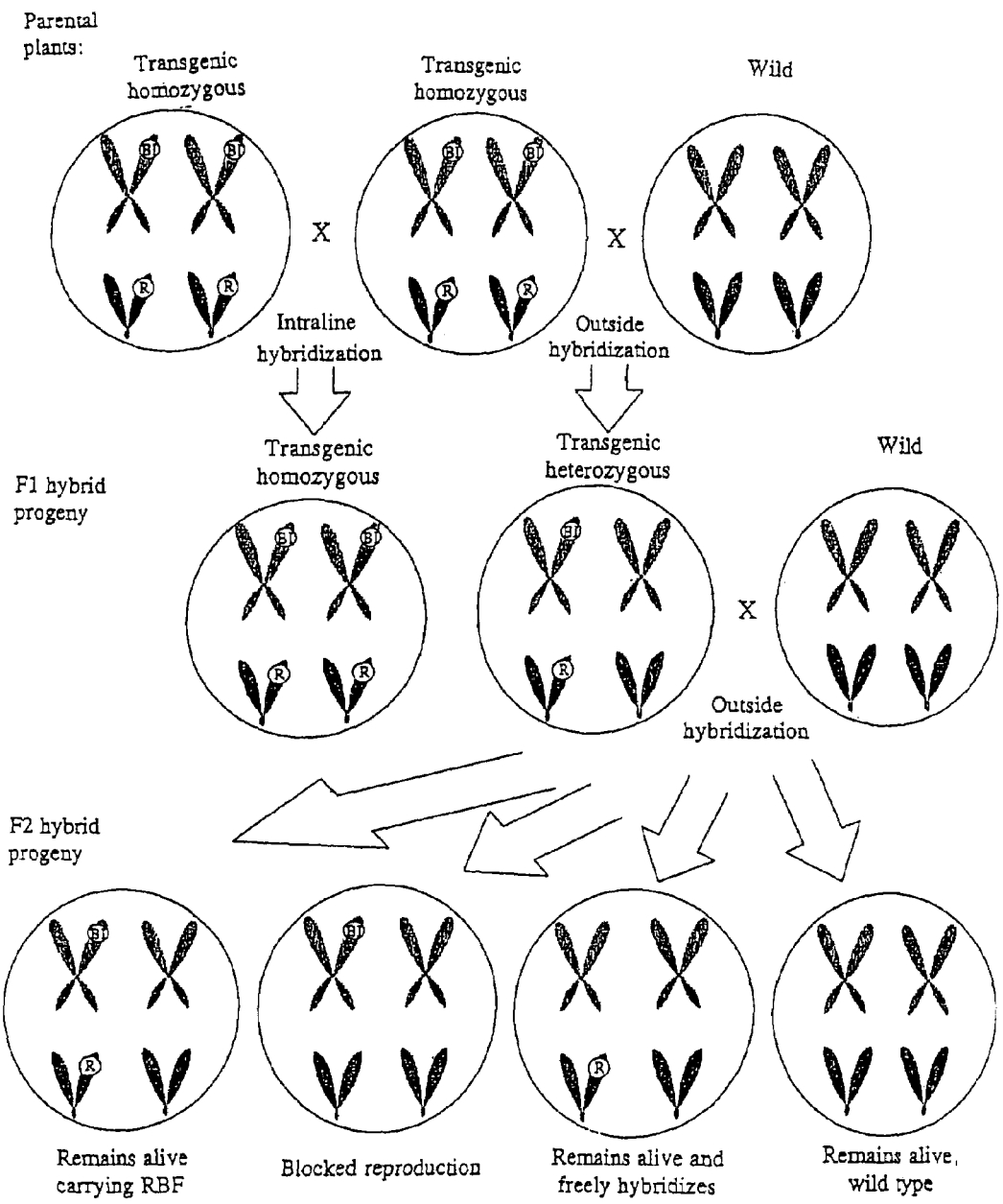
FIG. 13. illustrates schematically hybridization of transgenic plants carrying segregating RBF constructs. Blocking construct (here marked as B) and transgene of interest (here marked as I) are placed in different non-allelic chromosome than Recovering construct (here marked as R).

The BC and RC are positioned in different non-allelic chromosomes. Both of the constructs are in homozygous condition; BB (blocking construct) and RR (Recovering construct). Expression of both of the constructs may be constitutive, organ specific or development specific. Preferably, both of the constructs are expressed under the same kind of promoter. External regulation (artificial control) of the segregating RBF is performed by intraline crossing of the transgenic homozygous plants. Segregating RBF does not act in the first generation of outline hybridization because it will be in heterozygous condition BbRr (where b and r are recessive alleles which do not contain BC and RC, respectively) and thus both of the constructs act as in a homozygous parental line. The RBF starts to act from the second out breeding generation, when all the BbRr hybrids will die or have an altered feature because of lack of the recovering function. The RBF implies 50% negative selection of the TGI linked to the BC in each hybrid generation after the first hybrid progeny. FIG. 13 illustrates the mechanism of a segregating system.

Reversed Segregating RBF

Figure 14:
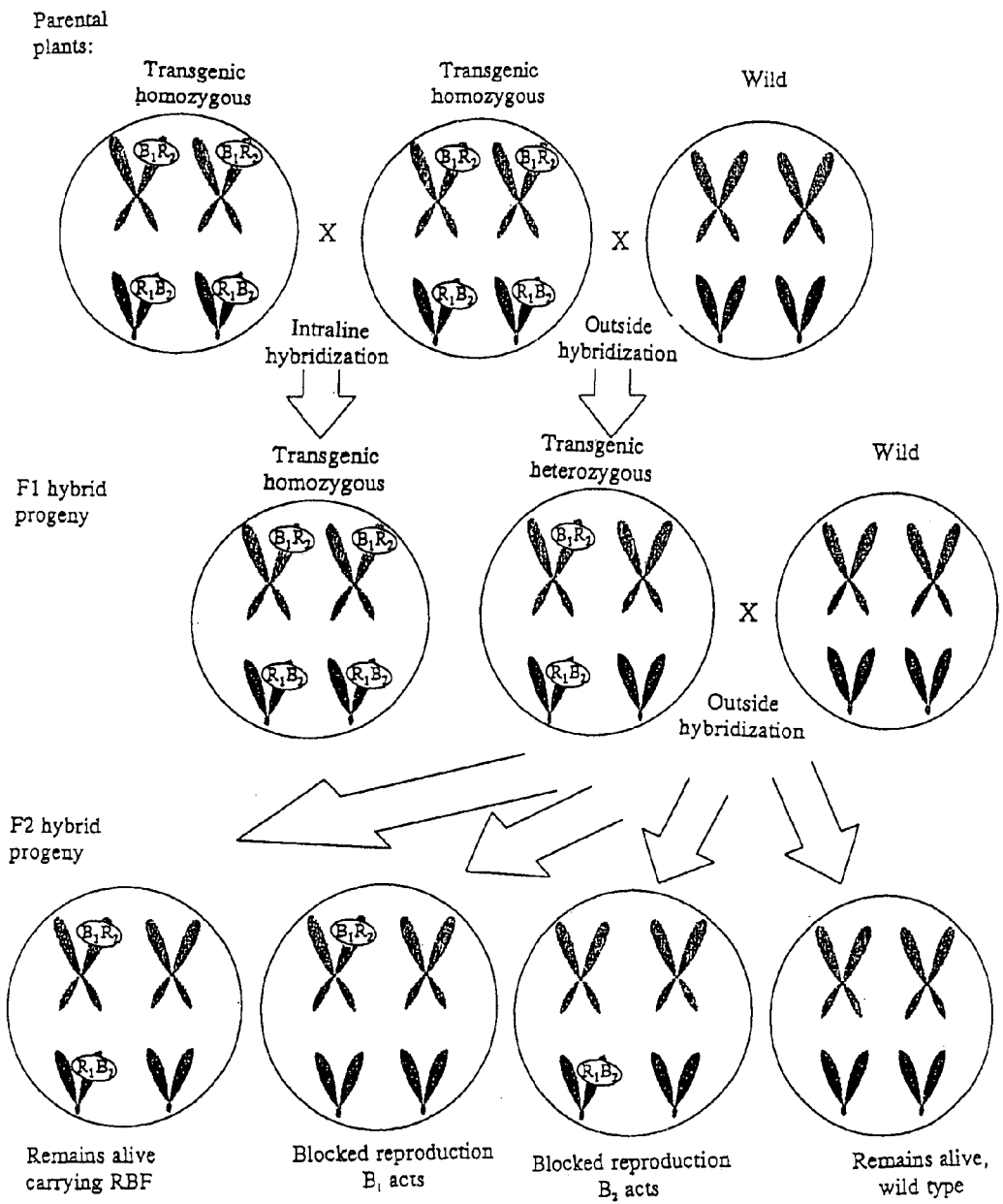
FIG. 14. illustrates schematically hybridization of transgenic plants carrying reverse segregating RBF constructs. The constructs of the first RBF is shown as B1 and R1 for blocking and recovering constructs, respectively. B2 and R2 constructs belong to the second RBF. The Blocking and Recovering constructs are placed in different non-allelic chromosomes in opposite order. Transgene of interest is not shown in the figure. It can be linked either to the first (B1) or the second (B2) blocking construct.

This system comprises two BCs and two RCs. It controls the release of both the BC and the RC. RC contains another blocking gene, which controls the release of the RC. The blocking gene action is recovered by a second RC, which is linked to a first BC and the TGI. Here we mark the construct alleles as follows: I—transgene of interest; B1—a first BC; B2—a second BC, which is different from the B1; R1—a first RC and; R2—a second RC. B1 acts in pair with R1 and B2 acts in pair with R2. The alleles B1B1IIR2R2 are situated in one pair of the allelic chromosomes and R1R1B2B2 are situated in another pair of allelic chromosomes. The first out-hybrid will carry B1b1IiR2r2 and R1r1B2b2 genotype. Thus, starting from the second out-hybrid generation the blocking construct (B1) will control the release of the transgene of interest (I), and the blocking construct (B2) will control the release of the recovering construct (R1). Therefore, this system controls the release of all the transgenic constructs from the plant. External control (or artificial treatment) comprises the action of intraline crossing to support the homozygous condition of transgenic plants (as in ordinary segregating RBF). The second recovering or blocking construct can be fused with first blocking or recovering construct in the same gene sequences as follows: B1 fused with R2 and B2 fused with R1. FIG. 14 illustrates the concept of a reversed segregating RBF.

Double RBF

The double RBF consists of two BCs. The BCs are placed in same transgenic insert and they are flanking the TGI from both sides. The functions blocked by expression of the BCs may be recovered by one or more RCs. Triple RBF is a segregating variation of the double construct.

The above-described RBF systems are described in the U.S. patent application 617,543, to which this disclosure is a continuation. The present disclosure provides an RBF system according to any of the above-described variations where the BC is placed inside an intron of the TGI. The present invention minimizes the probability of loss of control that could take place if BC is mutated or if a crossing over happens in between of BC and TGI. To minimize such a loss of control, we placed the coding sequence and polyadenylation signal of the blocking gene inside the intron of the TGI. Thus the BC cannot be separated from the active TGI as a result of DNA recombination. The majority of large mutations in the sequence of the BC would automatically lead to a simultaneous inactivation of the TGI.

The first challenge in reducing this concept into practice was the fact that according to the present knowledge introns of plant genes do not contain entire gene sequences.

To combine coding sequence, intron and polyadenylation signal in the intron cassette we had to use only minimal consensus signal sites and adapt barnase coding sequence to a high AT content. Successful combination of all components was only possible in a completely artificial synthetic sequence of the intron (SEQ ID NO: 3). Our construct is novel and has no analogous gene structures in plant nuclear genome.

Another challenge in reducing the concept into practice was to overcome the fact that the plant introns are mostly very short. Over two thirds of plant introns are less than 150 nt long and most of them are ranged from 80 to 139 nt. (Filipowicz et al 1995). It has been reported that the insertion of an intron at the end or downstream of coding sequence of the gene (in 3'UTR) can decrease expression of the gene. (Bourdon et al 2001). We used the GUS gene containing a small intron in the beginning of the gene. We inserted a large intron near the 3' end of coding sequence of the gene and surprisingly the level of GUS expression of our construct matched with that of a native GUS gene.

It is known from the prior art that dicot plants need all consensus signals and high AT content in their introns for a successful splicing. (Simpson and Filipowich 1996). Therefore we developed an intron using high AT content, 5' (AGGUAUGU) and 3' (GCAGG) signal sequences and placing branch point sequence (UACUAAC) 30 nucleotides upstream 3' splicing site. Approximately 50 nucleotides of exon near the splicing site were converted to a high GC content. We decided to use only short consensus signals of splicing, which was a challenge and not an obvious choice based on the prior art.

It is well known that the 5'UTR plays a significant role in gene expression. Usually a long 5'UTR is implicated in regulating gene expression. According to one embodiment of the present invention the mRNA of the modified barnase gene has a 50 nucleotides-long 5'UTR (SEQ ID NO: 5) which coincided with the last exon of GUS (SEQ ID NO: 4) and the 3' flanking signal of the intron (SEQ ID NO:6). The size of the last exon of GUS gene should be long enough to result in such a truncated GUS protein that cannot be able to maintain enzymatic activity in case of incorrect splicing of the intron. The 5'UTR sequence (SEQ ID NO: 5) has been checked for the absence of occasional start codons and TATA like sequences. Long nonsense 5'UTR, high AT content and ineffective polyadenylation could decrease barnase expression on posttranscriptional level. Furthermore, position effect may lead to variation in expression levels of the BC and the RC placed in different inserts.

The vicinity of TATA box may be modified without loosing promoter activity. Silencing can be induced by simultaneous expression of opposite strand corresponding to intron sequence of the gene. Therefore, according to another embodiment of the present invention to make the expression independent on need of unsynchronization and avoidance of silencing, the TGI and the gene inserted in its intron may share the same direction of transcription (FIG. 1C). In this case both genes could share the same polyadenylation site.

The following examples are set forth to illustrate the method and in no way limit the scope of the invention.

EXAMPLE 1

DNA Synthesis and Cloning

The Barstar gene originating from *Bacillus amyloliquefaciens* was synthesized according to plant codon preference with low AT content (SEQ ID NO: 2). We used the GUS (uidA) gene containing an intron at the start of coding sequence for designing the intron cassette. The intron cassette containing the second intron sequence of GUS (SEQ ID NO:3) (between SpeI and PstI sites) harboring the barnase gene (SEQ ID NO: 1) and the third exon of the GUS (SEQ ID NO: 4) was split into two segments. Each segment was synthesized from 55-59-base long oligonucleotides in high fidelity PCR. The two segments were then ligated in EcoRI restriction site (FIG. 2).

Heat shock promoter of *Glycine max* and cysteine endopeptidase (SH-EP) promoter of *Vigna mungo* were also cloned using a high fidelity PCR.

The tetracycline repressor sequence (tetR) was also cloned in high fidelity PCR from *E. coli* strain XL1 and placed under the control of the 35S promoter. The RBF construct shown in FIG. 1. was assembled and then cloned in a modified pGPTV-HPT vector.

The 35Sp3T promoter containing three tet operators around its TATA box was cloned using 120-base long 3' primer from 35S promoter of CaMV according to published sequence (SEQ ID NO: 7). A salicylate inducible promoter (Salp) was cloned from tobacco genome using PCR.

EXAMPLE 2

Design of the Intron Cassette

In this specific example we designed the Intron cassette so that barnase (BC) and GUS (TGI) genes are transcribed in opposite directions with respect to each other (FIG. 1A). Barnase coding sequence (SEQ ID NO: 1) was placed in the intron of GUS gene (FIG. 2). GUS gene was split in position 49 nucleotides upstream the stop codon. CGC codon of arginine has been changed to AGG to form splicing site between the two guanidines. Six nucleotides before the splicing site, a glutamine codon was changed from CAA to CAG to form a PstI restriction site. The sequence CGCTTTTCTG (SEQ ID NO: 8) upstream the PstI site was changed to TGCCTTCCTG (SEQ ID NO: 9) to introduce an additional alternative cleavage site for polyadenylation and to increase the GC content in the close vicinity of the intron. Restriction site PstI and the minor changes upstream of it were introduced by PCR amplification of GUS gene sequence using long 5' primer containing the modifications described above. The SH-EP promoter was modified after the natural SpeI restriction site. As shown in FIG. 2, the sequence spanning the SpeI site at −127 position and the PstI site at +367 position in the direction of the barnase gene sequence was synthesized using a high fidelity PCR.

Barnase codon bias was adapted for intron sequence by increasing the AT content, however, minor dicot codons were avoided. The gene is driven by SH-EP promoter whose sequences downstream of the SpeI site were modified to form the FUE element (AAACAT) of the polyadenylation recognition site as well as the end of the coding sequence of the GUS gene in complementary strand of DNA (changed nucleotides are underlined in FIG. 2). The SH-EP promoter was found to contain two natural tandem NUE-like repeats (TTATTTATTT) (SEQ ID NO:10) upstream SpeI site that could function as a polyadenylation signal for GUS in opposite chain. The third 52 nucleotide long exon of GUS gene (SEQ ID NO: 4) partially overlapped with the 39 bases at the 5' end of SH-EP promoter and partially with the 13 bases of the 5'UTR of barnase coding sequence. GUS intron 3' splicing signal (GCAGG) and consensus branch point sequences (UACUAAC) were introduced as a complementary strand of 5'UTR of barnase. Downstream of barnase coding sequence, polyadenylation signal sequences (FUE and NUE) were placed before GUS intron 5' splicing site. CA and TA polyadenylation cleavage sites of barnase were placed between the first and ninth nucleotide downstream of the PstI site. Accordingly, only 13–16 nucleotides of barnase and GUS mRNAs overlap in SH-EPp side and 12–20 nucleotides in 3' barnase side. To design Intron cassette, minimal consensus intron and polyadenylation sequences were used. Sequence of the intron was 72.4% AT rich, while the 50 bases of the neighboring exon of GUS have a 39.5% AT content.

EXAMPLE 3

Figure 4:
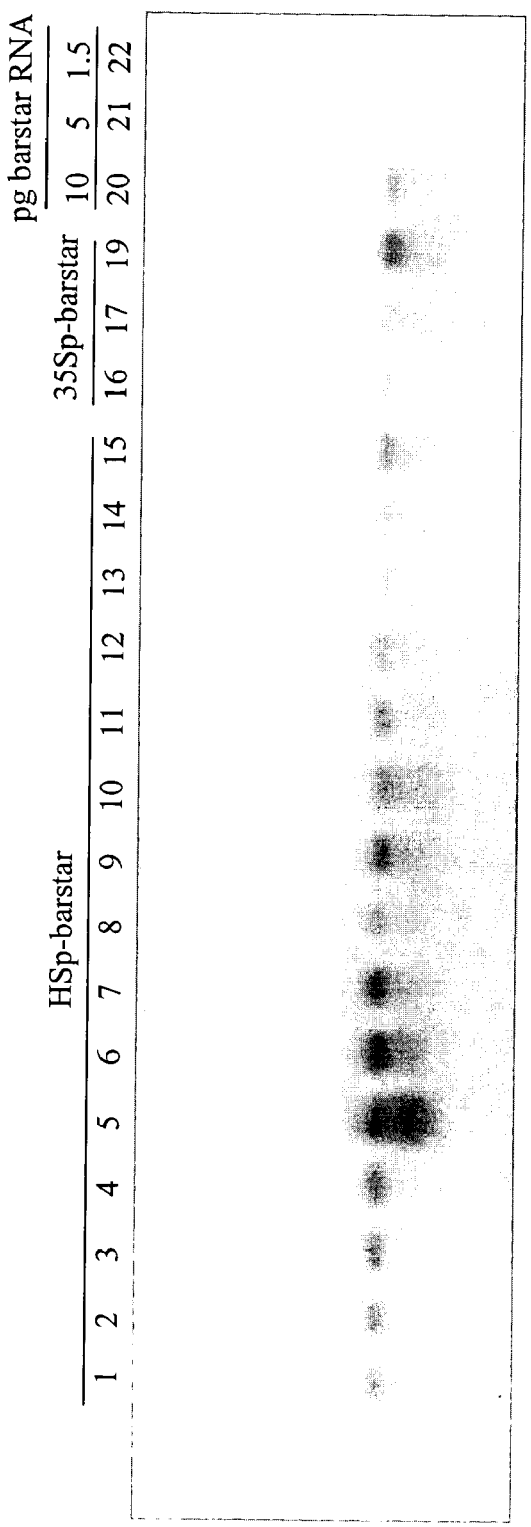
FIG. 4. Northern hybridization of Barstar expression in tobacco plants transformed by pGPTV-KAN-35SpBarstar. Lines 1 to 15 represent heat shock promoter containing transformant, which were treated at 40C for 1 hour. Lines 16 to 19 represent 35S promoter containing barstar transformants. Lines 20 to 22 represent unlabelled antisense barstar of 10, 5 and 1,5 pg.
Figure 5:
FIG. 5. PCR analysis of tobacco plants transformed with an Intron construct. Lines 15,16 and 17 representing the Int(−)HspStar are positive with both HYG and GUS gene.

A Segregating Type of RBF having an Intron Cassette with Organ Specific Expression of BC and Inducible Expression of TGI In order to achieve a segregating type of RBF we developed a DNA construct, where BC is situated in the intron of TGI and the RC is inserted in a different chromosome (FIG. 1*a* and *b*). The segregating RBF provides control for TGI containment after the RC segregates apart the construct carrying the TGI and the BC. After RC segregates apart, expression of the BC prevents the reproduction of plants carrying the TGI linked with BC. BC was placed under an organ-specific promoter, which in this example was cysteine endopeptidase (SH-EP) from *Vinga mungo*. Other organ-specific promoters could be used as well. A functional example of other promoters is Crusiferine promoter from *Brassica napus*.

In this example the RC was regulated by heat shock promoter of *Glycine max*, and thereby the RBF was heat shock inducible. Other heat shock promoters or could be used as well. 35S promoter from CaMV as well as 3 tet operators and tetR gene are also possible. Inducible RBF prevents the host plant reproduction until RC is induced by an outside stimulus, in this example a heat shock, at the time of BC expression.

The TGI and the BC were directed in opposite orientation in the intron cassette (FIG. 1*a*). To avoid a possible dsRNA silencing we used inducible expression of the TGI and organ-specific expression of BC. As an example we used GUS gene as the TGI. BC was barnase and RC was barstar in this specific example.

We developed two parallel constructs: 1) salicylate inducible construct (Sal) and 2) tetracycline inducible construct (Tet). The Sal construct includes Intron cassette with barnase driven by SH-EP promoter and GUS gene driven by salicylate inducible promoter FIG. 9 and FIG. 10.

The Tet construct contained the same Intron cassette but the GUS gene is now driven by a tetracycline inducible 35S promoter containing three tet operators around its TATA box. The construct also contains a tetracycline repressor gene (tetR) driven by the 35S promoter. The product of the gene binds to the tet operators repressing the expression of GUS gene. FIG. 12.

EXAMPLE 4

Bacteria and Plant Transformation

*Escherichia coli* strain XL1 was used for the cloning of the DNA constructs.

Leaf segments of tobacco plants (*Nicotiana tabacum*) cv. Samsung were inoculated with suspension of *A. tumefaciens* strain LBA4404 carrying the pGPTV-HPT and pGPTV-NPT binary vectors, which are based on pBIN19. Putative transformants were selected on 30 mg/l hygromycin or 75 mg/l kanamycin. The RC construct was transferred first and positive lines as revealed in Northern analysis (FIGS. 3 and 4) were re-transformed with the TGI containing the coding sequence of BC in its last intron. Selection of lines with successful second transformation was made on the basis of GUS and Northern analyses (FIG. 5). Positive lines were transferred to the greenhouse for further studies.

EXAMPLE 5

Analysis of Gene Expression

The gene expression assays were based on histological GUS assays. Fresh leaf materials were frozen in liquid nitrogen and then pulverizes into fine powder. The powder was homogenized in Na-phosphate buffer (50 mM Na-phosphate, pH 7.0; 10 mM EDTA; 0.1% Triton X-100; 14 mM 2-βMercaptoethanol). The homogenate was centrifuged for 10 min at 13000 g and the soluble crude protein in the supernatant was quantified using the Bradford method (Bio-Rad). The substrate p-Nitrophenyl-β-D-glucuronide was used to determine GUS activity. The substrate solution was added to the protein extracts to a final concentration of 1 mM and the mixture was incubated at 37° C. for 30 min. The absorbance of the developed color was measured with a spectrophotometer at 450 nm wavelength. A standard curve was drawn from data obtained from reactions of known concentration series of pure GUS enzyme. Protein extracts obtained from non-transgenic plants were used as a negative control. Amount of active GUS enzyme was calculated in pmols of processed substrate per 1 mg of total soluble protein per min.

To confirm transformation event, a PCR analysis of genomic DNA was performed. Primers were designed for amplification of fragments that ranged in length from 300 to 600 bp. Northern and Southern analyses were performed according to the supplier's recommendations (Boehringer Mannheim—Roche: 'The DIG user's guide for filter hybridization'). The intron-adapted barnase sequence, barstar and 600 bp central part of GUS were amplified using primers tailed with T7 promoter from the 5' end and SP6 promoter from the 3' end corresponding to a sense strand of the genes. The resulting PCR products were then used as templates for the synthesis of a Digoxigenin-labeled RNA probe as opposite strand and unlabeled control as a full-size sense strand. Unlabeled control RNA of the genes was mixed in different picogram amounts with 1–10 μg of total RNA of non-transgenic leaves or embryos and processed in parallel with the test RNA in Northern analysis to estimate transcription levels of the test genes. Total RNA preparations were isolated using the Qiagen RNeasy kit. 1 to 20 μg samples of total RNA were run in an agarose gel and electro-blotted (Genie Blotter by Idea Scientific) on a positively charged nylon membrane. The membrane was hybridized and developed according to the supplier's instructions (Boehringer Mannheim—Roche).

Reverse Transcription followed by PCR (RT-PCR) was performed according to the supplier's recommendations (Promega) using M-MLV Reverse Transcriptase, RNase H Minus, Point Mutant (Promega) and Thermo-Start® DNA Polymerase (Abgene). RNA was isolated from the leaf or embryonic tissues using 'RNeasy Plant Mini Kit' (Qiagen) and treated by RNase-Free DNase RQ1 (Promega) to remove residual traces of genomic DNA. RNA samples not incubated with M-MLV were used as negative control. Two specific primers were used for analysis of splicing site of GUS gene and for identification of barnase mRNA. For recognition of polyadenylation site, one 5'specific primer and poly-T primers (with/without 1–3 nucleotide anchors) were used. The RT-PCR products were cloned and sequenced.

Real Time PCR analysis was performed to support the RNA estimates obtained from the Northern analysis. Forward GUS-LcF primer: ATCAGCGTTGGTGGGAAA (SEQ ID NO:11) and reverse GUS-LcR primer: ACGAATATCTGCATCGGC (Proligo) (SEQ ID NO 12) were used. Total leaf RNA isolation and reverse transcription were performed as described above. In the reverse transcription step M-MLV Reverse Transcriptase, RNase H Minus, Point Mutant (Promega) and the Reverse primer GUS-LcR were used. The subsequent PCR step was performed using the LightCycler and a SYBR green dye according to supplier's instructions (Roche). The size of template amplified in Real-Time PCR was 92 bp. RNA samples not incubated with M-MLV were used as negative control. RNA isolated from non-transgenic tobacco was used as zero control to adjust for the unspecific background.

EXAMPLE 6

GUS Assays with Tet Plants Indicate that Neither the Intron Insertion Nor the Artificial Polyadenylation Signal does Decrease Gene Expression Eight tobacco lines carrying the Tet-construct expressed GUS, barnase and barstar genes in varying degrees. (Table 1) This suggests that the position of the genes have an effect on the expression. The lines vary in tetracycline regulation of GUS gene from very strict and weak expression to strong and constitutive. The level of GUS expression in Tet lines 5 and 8 was measured in quantitative GUS assay in comparison with transgenic tobacco plants expressing the GUS gene driven by the 35S promoter. These results clearly indicated that the Tet plants exhibited levels of GUS gene similar to intact 35S promoter driven expression (Table 1). These results clearly indicate that neither the intron insertion nor the artificial polyadenylation signals does decrease the gene expression.

TABLE 1

| GUS expression in quantitative GUS assay[a] | | | |
|---|---|---|---|
| Tobacco Line/construct | ±tetracyc. induction | The first assay | The second assay |
| Tet 3 | −tet | — | 0.0 |
| Tet 3 | +tet | — | 50.0 |
| Tet 5 | −tet | 2759.9 | 2367.2 |
| Tet 6 | −tet | 133.7 | — |
| Tet 6 | +tet | 326.0 | 1261.5[b] |
| Tet 8 | −tet | 39.7 | 212.6 |
| Tet 8 | +tet | 2551.7 | 3940.6[b] |
| 35Sp-GUS tobaccos[c] | −tet | 829.0 | 2096.0 |
| 35Sp-GUS tobaccos[c] | −tet | 3127.4 | 3944.7 |

[a]Expression of GUS enzyme is shown as pMol × min$^{-1}$ × μg$^{-1}$.
Induction of leaf segments was performed by 1 mg/l tetracycline for 3 days ([b]7 days).
[c]Tobacco plants expressing native GUS gene under natural 35S promoter.

EXAMPLE 7

Pollination, Germination and Heat Shock Experiments

Greenhouse grown tobacco plants were used in these experiments. Plants for self-pollination were grown in isolation. In pollination experiments, the transgenic tobacco pollens were used to pollinate wild type mother plants. The anthers were removed just before anthesis and the emasculated flowers were pollinated from pollens collected from transgenic plants soon after their stigmas get receptive. During flowering and seed set, these plants were kept at 25° C. at day time and at 20° C. at night time. The plants were incubated at 42° C. for 2 hours every second day. The harvested seeds were germinated on wet filter paper. In induction experiments germination proceeded on an aqueous media containing 1 mg/l tetracycline or 0.1 mM potassium salicylate

EXAMPLE 8

Germination Assays of Sal-Plants

In the germination assay we used seeds from self-pollinated greenhouse grown tobacco lines 15 and 17 (FIG. 5). The transgenic plants carrying the RBF construct showed normal phenotype: they grew, flowered and produced seedpods after self-pollination. Although the seeds collected from the plants were of normal size, they did not germinate. However, mother plants that were treated with the heat shock during seed development restored the germination function of F1 seeds. F1 seeds from crosses with non-transgenic plants also germinated when parent plants were heat-treated. Only 50% of the seeds from the normally growing non-transgenic crosses germinated suggesting Mendelian segregation RC from BC. (Table 2).

Figure 6:
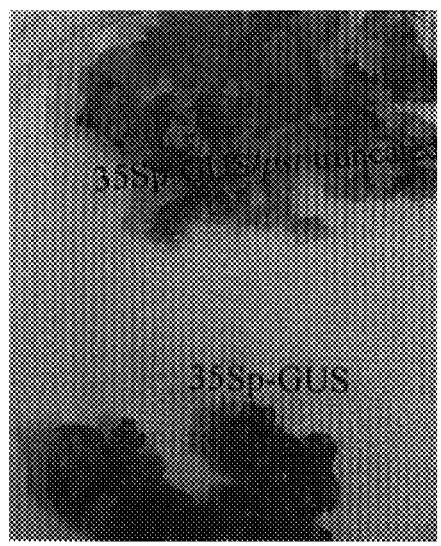
FIG. 6. Tobacco callus after transformation by 35SpGUS/Pst construct (above) and callus after transformation by 35SpGUS construct (below). Truncated GUS gene cannot produce active enzyme and therefore transformed callus does not show blue color.

Tobacco plants were transformed also with pGUS-int carrying LBA4404 Agrobacterium. After regeneration of selected shoots, some of the explants (from both transformations) were tested in a GUS assay. Those explants transformed by GUS/Pst did not show any positive reaction in the GUS test, as shown in FIG. 6. Five of the recovered transgenic shoots were tested for the presence of 35SpGUS/PSt insert using PCR and all of the five regenerates showed the presence of the insert in the genome.

Correct splicing and polyadenylation of GUS gene was substantiated by analyzing the sequences of the RT-PCR products. The assay detected also a second cryptic polyadenylation site situated 170 nucleotides downstream of the main (artificial) polyadenylation site (FIG. 2).

Due to the low level of expression of barnase in the embryos of tobacco plants, RT-PCR product was successfully cloned and sequenced using only specific primers designed for distal 5' and 3' sequences of barnase mRNA. Unspecific poly-T primers failed to produce the anticipated sequence. The analysis showed that full size barnase mRNA amount dominates that of the cryptic version. Correct size and level of expression of barnase mRNA in embryonic total RNA was also demonstrated in Northern analysis (FIG. 7A).

GUS gene expression level was measured in Northern analysis (FIG. 7B) and similar levels of expression were obtained from Real-Time PCR analysis. Expression of GUS gene ranged from 0.0 to 0.2 pg/µg of total RNA in the absence of tetracycline and from 0.5 to 40 pg/µg RNA following tetracycline treatment. Tet line No 5 showed a constitutive expression of GUS comparable to that expressed under the native 35S promoter, which was over 50 pg/µg of total RNA. GUS RNA expression levels perfectly matched with the quantitative results of the GUS assays (Table 1). No specific signal for GUS mRNA was detected with probe synthesized on the basis of the sequence of the second intron of GUS gene (FIG. 7C). This result together

TABLE 2

Germination assay of seeds of tobacco plants carrying Sal constructs.
NTS - non transgenic tobacco v. Samsung; HSp - transgenic tobacco carrying RC insert containing barstar driven by HS promoter; selfed—means self-pollinated.

| Construct and heat treatment Line 15 | Totat number of seeds | Germinated (G) | Ungerminated (U) | G/U |
|---|---|---|---|---|
| pInt(−) HSp x NTS, heat treated | 54 | 50 | 3 | 16/1 |
| pInt(−) HSp x NTS, heat untreated | 1040 | 560 | 480 | 1.1/1 |
| pInt(−) HSp selfed, heat treated | 975 | 971 | 4 | 197/1 |
| pInt(−) HSp selfed, heat untreated | 764 | 9 | 755 | 1/84 |
| pInt(−) HSp x NTS, heat treated | 205 | 187 | 18 | 10/1 |
| pInt(−) HSp x NTS, heat untreated | 1005 | 554 | 496 | 1.2/1 |
| pInt(−) HSp selfed, heat treated | 566 | 540 | 26 | 21/1 |
| pInt(−) HSp selfed, heat untreated | 688 | 2 | 686 | 1/343 |

EXAMPLE 9

Correct Splicing of Artificial Intron and Polyadenylation of TGI Containing BC In order to prove that an unspliced TGI gene is inactive, we designed the pGPTV-HPT-35SpGUS/Pst vector, wherein the GUS gene is truncated in the start site of the intron. This construct was cloned and transformed into tobacco plants. The vector was sequenced in the ATG codon region to confirm that translation start is fully functional.

with that of the RT-PCR showed that the artificial intron on the GUS gene was correctly spliced out.

In this example the intron cassette was designed in such a way that barnase and GUS genes are transcribed in opposite direction with respect or one another. Barnase coding sequence was placed in the intron of GUS gene. Gus gene was split in position 49 nucleotides upstream the stop codon. CGC codon of arginine has been changed to AGG to form splicing site between the two guanidines. Six nucleotides before the splicing site, a glutamine codon was changed from CAA to CAG to rom a PstI restriction site. The sequence CGCTTTTCTG (SEQ ID NO: 8) upstream the PstI site was changed to TGCCTTCCTG (SEQ ID NO. 9) to introduce an additional alternative cleavage site for polyadenylation and to increase the GC content in the close vicinity of te intron. Restriction site PstI and the minor changes upstream of it were introduced by PCR amplification of GUS gene sequence using long 5' primer containing the modifications described above. The cysteine endopeptidase (SH-EP) promoter was modified after the natural SpeI restriction site. As shown in FIG. 2, the sequence spanning the SpeI site at −127 position and the Pst I site at +367 position in the direction of the barnase gene sequence was synthesized using a high fidelity PCR.

In order to prove that an unspliced TGI gene is inactive, we designed the pGPTV-HPT-35SpGUS/Pst vector, wherein the GUS gene is truncated in the start site of the intron. This construct was cloned and transformed into tobacco plants. The vector was sequenced in the ATG codon region to confirm that translation start is fully functional.

Tobacco plants were transformed also with pGUS-int carrying LBA4404 Agrobacterium. After regeneration of selected shoots, some of the explants (from both transformations) were tested in a GUS assay. Those explants transformed by GUS/Pst did not show any positive reaction in the GUS test, as shown in FIG. 6. Five of the recovered transgenic shoots were tested for the presence of 35SpGUS/PSt insert using PCR and all of the five regenerates showed the presence of the insert in the genome.

EXAMPLE 10

Synthetic Polyadenylation Sites Functioned Exactly and do not have Negative Effects on the Expression RNA polymerase termination and polyadenylation sites in plant genes have less consensus sequences than other signals. Therefore, the use of minimal FUE and NUE sequences had a risk to decrease expression of the genes in the event of improper polyadenylation. We have demonstrated in RT-PCR that polyadenylation of GUS occurred in the predicted site. The full sequence of barnase mRNA also has been revealed from cDNA. Expression and biological action of the genes were also effective. Therefore, the developed synthetic polyadenylation sites functioned exactly and did not have any negative effect on the expression.

EXAMPLE 11.

Figure 7:
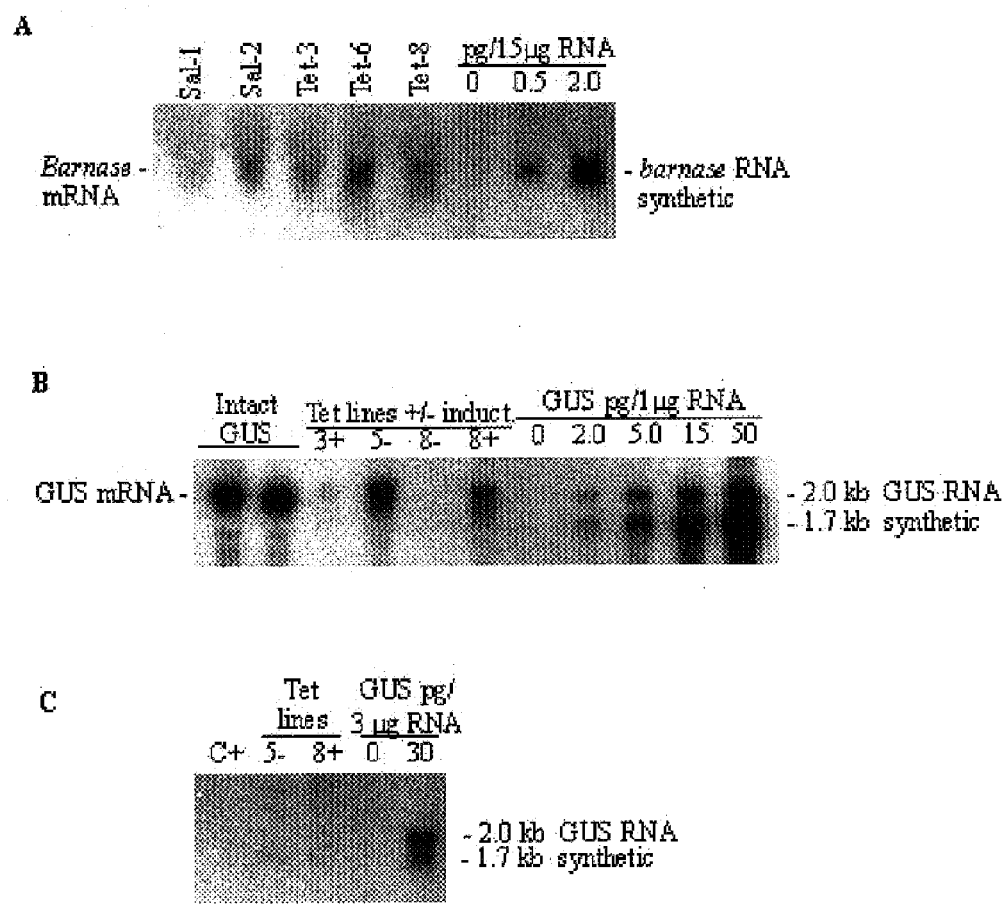
FIG. 7. Northern analysis of expression of barnase and GUS gene on Intron cassette.
  (A) Expression of barnase in tobacco embryos. 15 µg of embryo total RNA isolated form plants of Sal and Tet lines and unlabelled barnase control RNA mixed with 15 µg of non-transgenic carrier embryo total RNA were hybridized with barnase RNA probe.
  (B) Expression of GUS gene in tobacco leaves. 1 µg of leaf total RNA and unlabelled GUS control RNA of the sizes mixed with carrier RNA were hybridized with RNA probe of central part of GUS gene. The lines art shown treated (+) and untreated (−) with tetracycline.
  (C) Splicing of GUS gene. 3 µg of total leaf RNA and unlabelled GUS control RNA of two sizes mixed with carrier RNA hybridized with sense barnase RNA probe. C+ total RNA of tobacco expressing intact GUS gene. Absence of specific signal indicates successful splicing of the GUS gene in Tet lines 5 and 8.

TATA Box Vicinity did not Contain Regulatory Sequences and the Sequences can be Changed without Substantial Effect on Level and Specificity of Expression of the Promoter The modification TATA box vicinity of SH-EP promoter did not affect the barnase expression level according to our Northern analysis. FIG. 7.

The expression level corresponded to the expression of the high GC barnase gene under the native SH-EP promoter. The specificity of the SH-EP promoter also remained similar. The main peak of the promoter expression occurred at the stage of embryo development, and the resulting biological effect was observed during germination assays of Sal lines. Line 3 of the Tet construct expressed barnase in a strong and less specific manner, which resulted in dropping of fruits after flowering without heat shock. Line 3 also clearly exhibited a second peak of expression of the SH-EP promoter during germination. The data evidences that TATA box vicinity often does not contain regulatory sequences and the sequences can be changed without substantial effect on the level and specificity of expression of the promoter.

EXAMPLE 12

Figure 8:
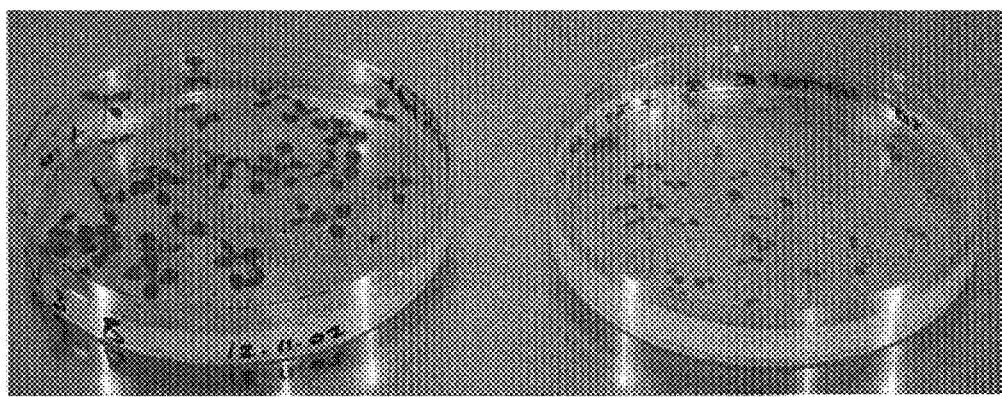
FIG. 8. Effect of heat shock on germination of seedlings of Tet line 3. Two-week old in vitro seedlings growing at room temperature are on the right. On the left, the seedlings were growing in the same conditions but incubated additionally at 42° C. for one hour at the age of one week. The briefly applied heat shock has induced barstar expression, which mitigated the negative effect of barnase.
Figure 9:
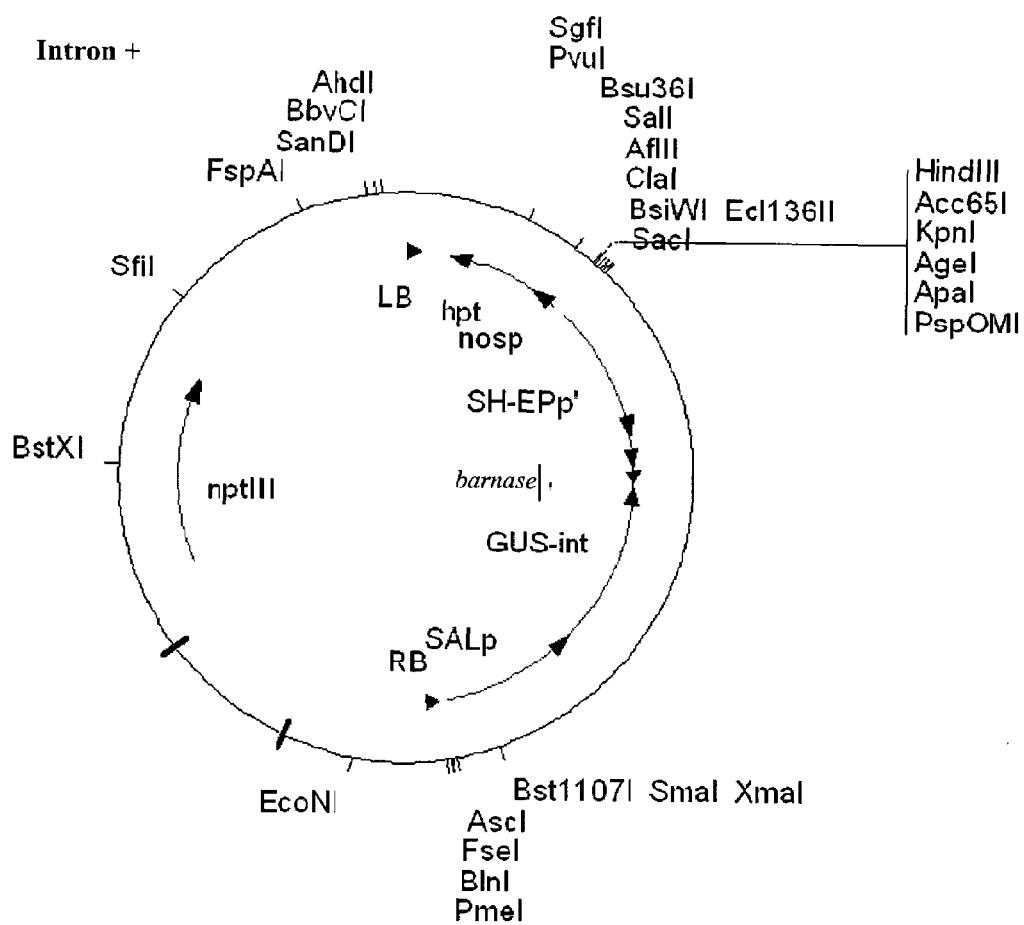
FIG. 9. pInt-Salp vector carrying Intron(Salp)+ construct.
Figure 10:
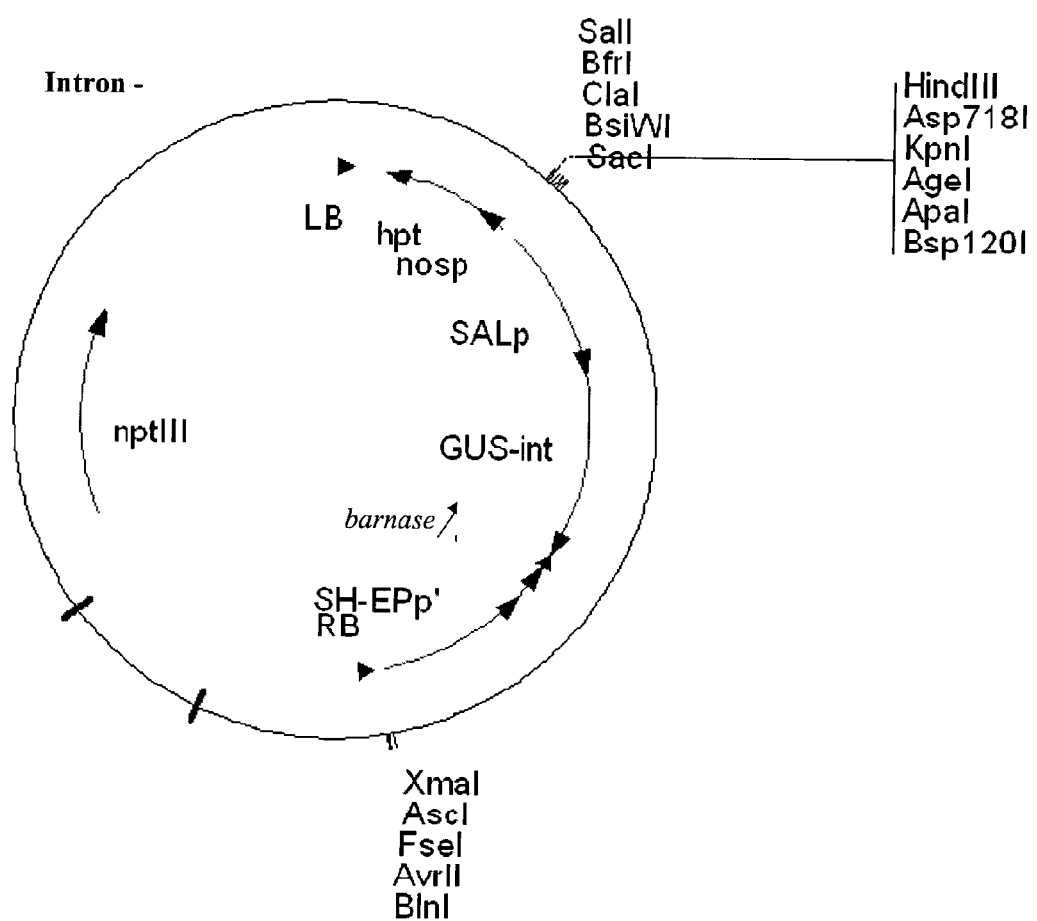
FIG. 10. pInt-Salp vector carrying Intron(Salp)− construct.
Figure 11:
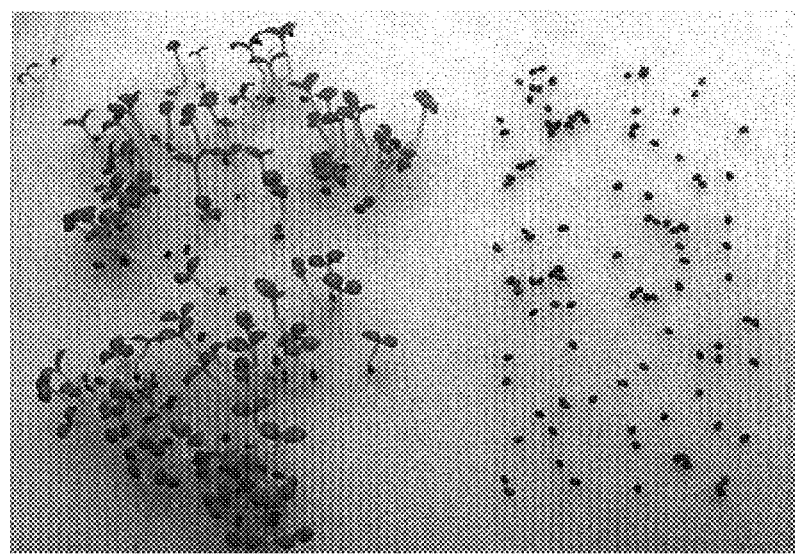
FIG. 11. Germination assay of tobacco seeds transformed with Intron(−)HSp-Barstar construct. On the left hand side seeds of transgenic tobacco plants were heat treated during seedpod maturation for 1 hour every second day. On the right hand side seeds of transgenic tobacco plants without heat treatment.
Figure 12:
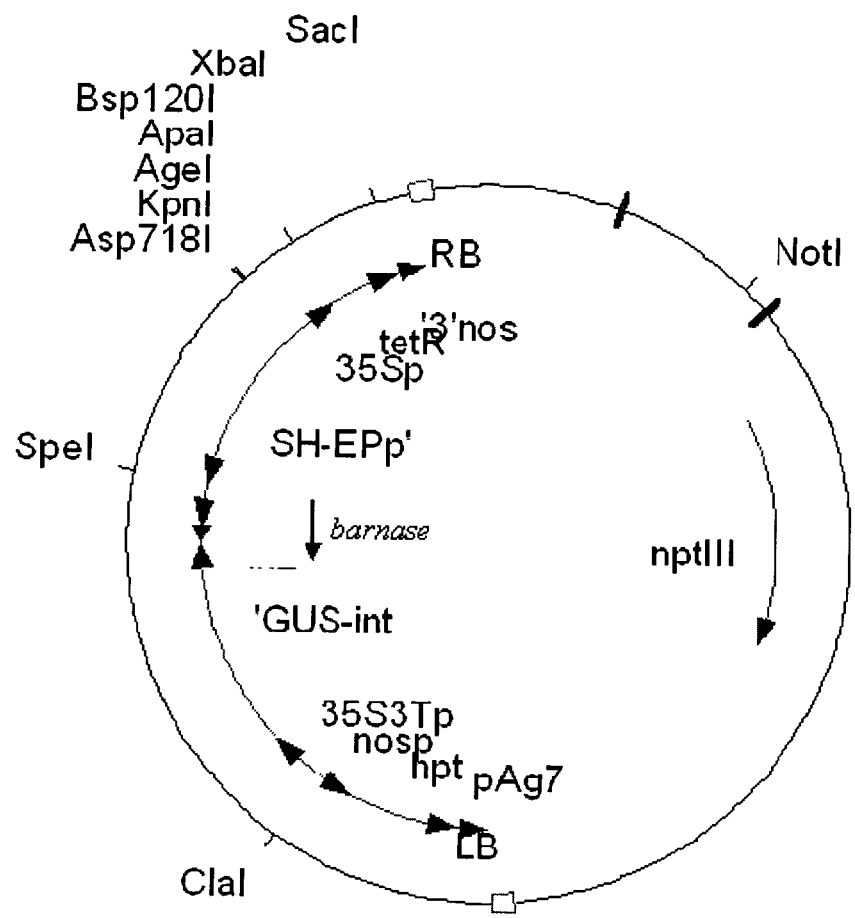
FIG. 12. pInt-Tet vector carrying Tet construct and Intron cassette.

Unsynchronization of GUS and Barnase Expression Allowed Avoiding dsRNA Formation and Silencing Specific germination/tetracycline induction test on seeds of Tet line 3 showed induced silencing effect. Positive heat shock effect on slowly germinating seedlings of Tet line 3 demonstrated the second peak of barnase expression. (FIG. 8) The self-pollinated seeds of Tet line 3 were germinated for 10 days in water or in solution having tetracycline 1 mg/l. The seeds germinating in water were exposed to 1 mg/l tetracycline for another 5 days. Seedlings were then tested in GUS activity. None of the seedlings that germinated in the presence of tetracycline did show GUS expression, whereas 25 to 50% of seeds germinating on water showed GUS activity. GUS gene expression level varied in intensity from high to weak. These results propose that the simultaneous expression of GUS and barnase genes during the first week of germination may result in dsRNA formation and sense-antisense silencing.

If GUS expression was induced after the barnase mRNA transcription has ceased, GUS mRNA and GUS enzyme activity remained stable. Unsynchronization of GUS and barnase expression allowed avoiding dsRNA formation and silencing. To make the expression independent on need of unsynchronization and avoidance of silencing, the transgene of interest and the gene inserted in its intron may share the same direction of transcription as shown in FIG. 1c. In such a case both the genes could share the same polyadenylation site.

It should be understood that many changes and modifications may be made to the details of the above-described preferred embodiment of the present invention without departing from the underlying principles thereof. The scope of the present invention should, therefore, be determined by the following claims.

What is claimed is:

1. A molecular mechanism for gene containment in sexually reproducing transgenic plants by providing a plant with a recoverable block of function (RBF) system, said system comprising:

a transgene of interest (TGI) encoding desired gene products;

a blocking construct (BC) having a capacity to block at least one molecular or physiological function essential for development or reproduction of the transgenic plant, thereby leading to death or incapacity of sexual reproduction, said BC being fully inserted into an intron of the TGI, said BC comprising a barnase coding sequence, which is operably linked to an embryo/germination specific promoter; and an externally controllable recovering construct (RC) being able to recover the functions blocked by the BC, said RC comprising a barstar coding sequence which is operably linked to a heat shock promoter.

2. The mechanism according to claim 1, wherein the BC and the RC are located in different chromosomes.

3. The mechanism according to claim 1, wherein the BC and the RC are located in same inserts.

4. The mechanism according to claim 1, wherein the barnase is encoded by a synthetic nucleotide sequence comprising SEQ ID NO:1.

5. The mechanism according to claim 1, wherein the barstar is encoded by a synthetic nucleotide sequence comprising SEQ ID NO:2.

6. The mechanism according to claim 1, wherein the BC and the TGI are positioned in different directions.

7. The mechanism according to claim 1, wherein the BC and TGI are positioned in same direction and are sharing a polyadenylation site.

8. The mechanism according to claim 1, wherein the embryo/germination specific promoter is a cysteine endoDeDtidase (SH-EP) promoter.

9. The mechanism according to claim 1, wherein the TGI is driven by an inducible or constitutive promoter.

10. A complex of DNA constructs comprising:
a TGI encoding desired gene products;
a BC having a capacity to block at least one molecular or physiological function essential for development or reproduction of a transgenic plant containing said BC, thereby leading to death or incapacity of sexual reproduction, said BC being inserted fully into an intron of the TGI, said BC comprising a barnase coding sequence which is operably linked to an embryo/germination specific promoter; and
an externally controllable RC being able to recover the functions blocked by the BC, said RC comprising a barstar coding sequence which is operably linked to a heat shock promoter.

11. The complex of DNA constructs according to claim 10, wherein the BC and the RC are located in different chromosomes.

12. The complex of DNA constructs according to claim 10, wherein the BC and the RC are located in same inserts.

13. The complex of DNA constructs according to claim 10, wherein the barnase is encoded by a nucleotide sequence comprising the SEQ ID NO:1.

14. The complex of DNA construct according to claim 10, wherein the barstar is encoded by a nucleotide sequence comprising the SEQ ID NO:2.

15. The complex of DNA constructs according to claim 10, wherein the BC and the TGI are in different directions.

16. The complex of DNA constructs according to claim 10, wherein the BC and TGI are positioned in same direction and share a polyadenylation site.

17. The complex of DNA constructs according to claim 10, wherein the embryo/germination specific promoter is an SH-EP promoter.

18. The complex of DNA constructs according to claim 10, wherein the TGI is driven by an inducible or constitutive promoter.

19. A transgenic plant comprising the complex of DNA constructs according to claim 10.

20. A transgenic cell line comprising the complex of DNA constructs according to claim 10.

* * * * *

SEQUENCE LISTING

<160> NUMBER OF SEQ ID NOS: 13

<210> SEQ ID NO 1
<211> LENGTH: 357
<212> TYPE: DNA
<213> ORGANISM: artificial sequence -continued
<220> FEATURE:
<223> OTHER INFORMATION: Plant adapted synthetic coding sequence of
      barnase gene

<400> SEQUENCE: 1
cgcggatcca tggcacaagt tatcaacacc tttgatggag ttgctgacta ccttcagacc    60
taccataagc ttccagataa ctacatcacc aagtctgagg ctcaggctct tggatgggtt   120
gcttctaagg gaaaccttgc tgatgtcgct ccaggaaagt ctatcggagg tgatatcttc   180
tctaacaggg agggaaagct tccaggaaag tctggaagga cctggaggga ggctgatatc   240
aactacacct ctggattcag gaactctgat aggatccttt actcttccga ctggcttatc   300
tacaagacca ctgaccacta ccagaccttc accaagatcc ggtgagagct cgagcgc      357

<210> SEQ ID NO 2
<211> LENGTH: 299
<212> TYPE: DNA
<213> ORGANISM: artificial sequence
<220> FEATURE:
<223> OTHER INFORMATION: Plant adapted synthetic coding sequence of
      barstar gene

<400> SEQUENCE: 2
cgcggatcct gatcatgaag aaggctgtta tcaacggtga gcaaattagg tctatctctg    60
atcttcacca gacccttaag aaggagcttg ctcttccaga gtactacgga gagaaccttg   120
atgctctatg ggattgcctt accggatggg tggagtaccc acttgttttg gagtggaggc   180
agtttgagca gtctaagcag cttactgaga atggagctga gagtgttctt caggttttcc   240
gggaggctaa ggctgaggga tgcgatatca ccatcattct ttcttgagag ctcgagcgc    299

<210> SEQ ID NO 3
<211> LENGTH: 529
<212> TYPE: DNA
<213> ORGANISM: artificial sequence
<220> FEATURE:
<223> OTHER INFORMATION: intron of uidA gene

<400> SEQUENCE: 3
actagtttac aaacgtttcc ctatataaac cctcctttgt tcactgcttt cctccctgct    60
gtggcttctc tccgaagttc atcccggtcc acctgcaaaa taagtaataa gataaagtaa   120
aaaagttagt atggctcaag ttattaatac ttttgatgga gttgctgatt atcttcaaac   180
ttatcataaa cttccagata attatattac taaatctgaa gctcaagctc ttggatgggt   240
tgcttctaaa ggaaatcttg ctgatgttgc tccaggaaaa tctattggag agatatttt   300 ttcaaataga gaaggaaaac ttccaggaaa atctggaaga acatggagag aagctgatat   360
taattatact tctggatta gaaattcaga tagaatcctt tattcatctg attggcttat   420
ttataaaact acagatcatt atcaaacttt tacaaaaatt agataaatat ttgtattttt   480
tgtatgttgt gatcattaat aaataaataa atacatacct cttctgcag              529

<210> SEQ ID NO 4
<211> LENGTH: 38
<212> TYPE: DNA
<213> ORGANISM: artificial sequence
<220> FEATURE:
<223> OTHER INFORMATION: 3' flanking signal of the intron of uidA

<400> SEQUENCE: 4
actaactttt ttactttatc ttattactta ttttgcag    38

```
<210> SEQ ID NO 5
<211> LENGTH: 474
<212> TYPE: DNA
<213> ORGANISM: artificial sequence
<220> FEATURE:
<223> OTHER INFORMATION: 35 S promoter of CaMV

<400> SEQUENCE: 5
gcggaattca attgatcaac atggtggagc acgacactct cgtctactcc aagaatatca      60
aagatacagt ctcagaagac cagagggcta ttgagacttt tcaacaaagg gtaatatcgg     120
gaaacctcct cggattccat tgcccagcta tctgtcactt catcgaaagg acagtagaaa     180
aggaagatgg cttctacaaa tgccatcatt gcgataaagg aaaggctatc gttcaagaat     240
gcctctaccg acagtggtcc caaagatgga ccccacccca cgaggaacat cgtggaaaaa     300
gaagacgttc caaccacgtc ttcaaagcaa gtggattgat gtgatatctc cactgacgta     360
agggatgacg cacaatccca ctatactcta tcactgatag agtctatata agactctatc     420
actgatagag tgaactctat cactgataga gtcgacggat ccatggaatc cgcg           474

<210> SEQ ID NO 6
<211> LENGTH: 10
<212> TYPE: DNA
<213> ORGANISM: artificial sequence
<220> FEATURE:
<223> OTHER INFORMATION: sequence upstream the PstI site

<400> SEQUENCE: 6
cgcttttctg                                                             10

<210> SEQ ID NO 7
<211> LENGTH: 10
<212> TYPE: DNA
<213> ORGANISM: artificial sequence
<220> FEATURE:
<223> OTHER INFORMATION: changed sequence upstream the pstI site

<400> SEQUENCE: 7
tgccttcctg                                                             10

<210> SEQ ID NO 8
<211> LENGTH: 10
<212> TYPE: DNA
<213> ORGANISM: artificial sequence
<220> FEATURE:
<223> OTHER INFORMATION: polyadenylation signal in transcription unit
      near the upstream element (NUE)

<400> SEQUENCE: 8
ttatttattt                                                             10

<210> SEQ ID NO 9
<211> LENGTH: 18
<212> TYPE: DNA
<213> ORGANISM: artificial sequence
<220> FEATURE:
<223> OTHER INFORMATION: Forward GUS-LcF  primer

<400> SEQUENCE: 9
atcagcgttg gtgggaaa                                                    18

<210> SEQ ID NO 10
<211> LENGTH: 18
<212> TYPE: DNA
```

```
<213> ORGANISM: artificial sequence
<220> FEATURE:
<223> OTHER INFORMATION: reverse GUS-LcR primer

<400> SEQUENCE: 10
acgaatatct gcatcggc                                                    18

<210> SEQ ID NO 11
<211> LENGTH: 716
<212> TYPE: DNA
<213> ORGANISM: artificial sequence
<220> FEATURE:
<223> OTHER INFORMATION: Vigna mungo (SH-EP promoter), Bacillis
      amyloliquefaciens (barnase gene), Esherichia coli (uidA gene)

<400> SEQUENCE: 11
tattgaatcc tttggctacc attcttgaga aacacaaaca cttcttatat ctgttctaca      60
caattctctg agtgcgtgcc acagtttggt atcttcatga ttgctcattg ttcatgccca     120
taaggaacat gtaacttcct catttattta ttattgcttt tgttttcttc tcactagttt     180
acaaacgttt ccctatataa accctccttt gttcactgct ttcctccctg ctgtggcttc     240
tctccgaagt tcatcccggt ccacctgcaa aataagtaat aagataaagt aaaaaagtta     300
gtatggctca agttattaat acttttgatg gagttgctga ttatcttcaa acttatcata     360
aacttccaga taattatatt actaaatctg aagctcaagc tcttggatgg gttgcttcta     420
aaggaaatct tgctgatgtt gctccaggaa aatctattgg aggagatatt ttttcaaata     480
gagaaggaaa acttccagga aaatctggaa gaacatggag agaagctgat attaattata     540
cttctggatt tagaaattca gatagaattc tttattcatc tgattggctt atttataaaa     600
ctacagatca ttatcaaact tttacaaaaa ttagataaat atttgtattt tttgtatgtt     660
gtgatcatta ataataaat aaatacatac ctcttctgca gcaggaaggc agccga         716

<210> SEQ ID NO 12
<211> LENGTH: 52
<212> TYPE: DNA
<213> ORGANISM: artificial sequence
<220> FEATURE:
<223> OTHER INFORMATION: the last (third exon) of uiD gene

<400> SEQUENCE: 12
gtggaccggg atgaacttcg gagagaagcc acagcaggga ggaaagcagt ga              52

<210> SEQ ID NO 13
<211> LENGTH: 51
<212> TYPE: DNA
<213> ORGANISM: artificial sequence
<220> FEATURE:
<223> OTHER INFORMATION: 5'UTR of barnase gene

<400> SEQUENCE: 13
catcccggtc cacctgcaaa ataagtaata agataaagta aaaaagttag t               51
```